United States Patent [19]

Holan et al.

[11] Patent Number: 4,849,450
[45] Date of Patent: Jul. 18, 1989

[54] NEW ARTHROPODICIDES

[75] Inventors: George Holan, Brighton; Reimund A. Walser, Box Hill; Bryan C. Elmes, Malvern, all of Australia

[73] Assignee: Dunlena Pty. Ltd., North Sydney, Australia

[21] Appl. No.: 44,765

[22] Filed: May 1, 1987

Related U.S. Application Data

[63] Continuation of Ser. No. 668,378, Oct. 2, 1984, abandoned.

[30] Foreign Application Priority Data

Mar. 2, 1983 [AU] Australia ............................... PF8267

[51] Int. Cl.$^4$ ................. C07C 69/757; C07C 121/66; A01N 31/14
[52] U.S. Cl. .................................... 514/521; 514/345; 514/532; 546/300; 546/301; 546/302; 558/406; 560/18; 560/59; 560/102
[58] Field of Search ........................ 546/301; 558/406; 560/18, 59, 102; 514/345, 521, 532

[56] References Cited

U.S. PATENT DOCUMENTS

| 4,264,606 | 4/1981 | Ozawa et al. | 546/301 |
|---|---|---|---|
| 4,277,490 | 7/1981 | Holan et al. | 514/532 X |
| 4,339,458 | 7/1982 | Holan et al. | 514/532 X |
| 4,348,409 | 9/1982 | Holan et al. | 424/308 |
| 4,360,690 | 11/1982 | Fuchs et al. | 560/18 X |
| 4,390,715 | 6/1983 | Holan et al. | 560/102 X |
| 4,391,820 | 7/1983 | Holan et al. | 560/102 X |
| 4,540,710 | 9/1985 | Holan et al. | 514/521 |

FOREIGN PATENT DOCUMENTS

| 0109934 | 5/1984 | European Pat. Off. | 546/301 |
|---|---|---|---|
| 0115689 | 9/1980 | Japan | 546/301 |

OTHER PUBLICATIONS

Mues, et al., C.A. 91: 39156, (1979).
Geuter, et al., C.A. 88: 152264u, (1978).
Holan, et al., C.A. 94: 103024f (1981).
Holan, et al., C.A. 92: 41589s and 92: 41591m, (1980).

*Primary Examiner*—Joseph Paul Brust
*Attorney, Agent, or Firm*—Bacon & Thomas

[57] ABSTRACT

Compounds with arthropodicidal activity having the general formula (I);

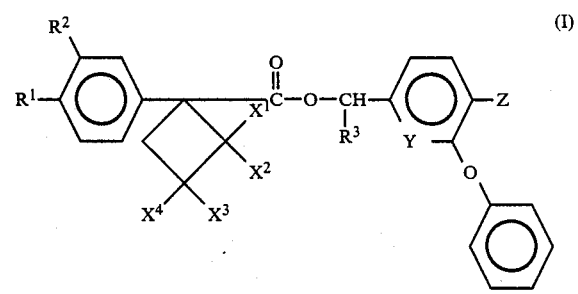

wherein $R^1$ is a halo group; or a lower alkyl, lower alkoxy or lower alkylthio group, in each of which the alkyl group may be substituted with one or more halo groups; $R^2$ is hydrogen or a halo or methyl group; or $R^1$ and $R^2$ together form a methylenedioxy, or a difluoro-methylenedioxy group or, $R^1$ and $R^2$ together with the carbon atoms to which they are attached, form an aromatic ring; $R^3$ is hydrogen, CN, or C≡CH; Y is —CH— or —N—; Z is H or F; and $X^1$, $X^2$, $X^3$, and $X^4$ are the same or different and each is hydrogen or a fluoro, bromo or chloro group; with the proviso that Y is —N— when Z is H.

9 Claims, No Drawings

NEW ARTHROPODICIDES

This is a continuation of application Ser. No. 668,378, filed 10/2/84, now abandoned.

This invention relates to new compounds having arthropodicidal activity, to methods of preparing these compounds and to the use of the compounds as arthropodicides, especially as insecticides and acaricides.

The compounds provided by this invention have the general formula (I):

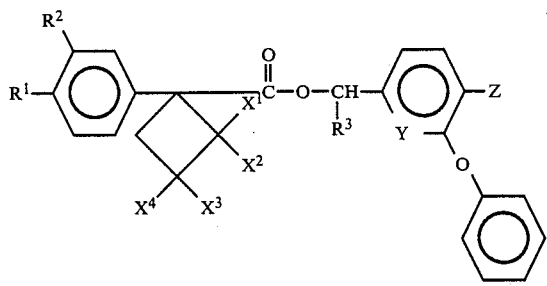

wherein $R^1$ is a halo group; or a lower alkyl, lower alkoxy or lower alkylthio group, in each of which the alkyl group may be substituted with one or more halo groups;

$R^2$ is hydrogen or a halo or methyl group; or $R^1$ and $R^2$ together form a methylenedioxy, or a difluoromethylenedioxy group or, $R^1$ and $R^2$ together with the carbon atoms to which they are attached, form an aromatic ring;

$R^3$ is hydrogen, CN, or C≡CH;

Y is —CH— or —N—;

Z is H or F; and $X^1$, $X^2$, $X^3$, and $X^4$ are the same or different and each is hydrogen or fluoro, bromo or chloro group; with the proviso that Y is —N— when Z is H.

As used herein "halo" means fluoro, chloro or bromo; "lower" implies alkyl groups having from 1 to 4 carbon atoms. Alkyl groups having more than 2 carbon atoms may be straight or branched.

Related prior art compounds disclosed in our Australian Patent Specification Nos. 530,169 (42723/78) and 525,002 (53362/79), are esters of acids of the general formula (II)

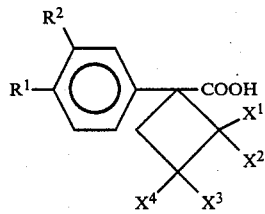

wherein $X^1$–$X^4$, $R^1$ and $R^2$ are essentially as defined above with one of the following alcohols:
3-phenoxybenzyl alcohol
α-cyano-3-phenoxybenzyl alcohol
α-ethynyl-3-phenoxybenzyl alcohol
α-cyano-3-(4-chlorophenoxy)benzyl alcohol Compounds similar to those of formula (I) but where the cyclobutane moiety is replaced by a cyclopropane moiety and where $R^3$=H, Y=CH and Z=F are disclosed in Australian Patent Specification No. 72456/81.

It will be readily appreciated by those skilled in the art that the obvious structural differences between the prior art compounds and those of the present invention (formula (I)) will give rise to significant differences in insecticidal properties, both in level of activity in individual insect species and in the spectrum of activity against various species. Such differences, however, are not readily predictable either as to magnitude or sign.

The compounds of the invention (formula (I)) are optically active and can be resolved into their optical isomers by conventional methods. The invention thus includes the individual optical isomers of the compounds as well as the racemic forms.

The compounds of formula (I) may be prepared by the conventional methods of synthetic organic chemistry.

For example, the compounds of formula (I) may be formed by reacting an acid of formula (II) as stated above, wherein $R^1$, $R^2$ and $X^1$–$X^4$ are as defined above, or a reactive derivative of said acid with an alcohol of formula (III)

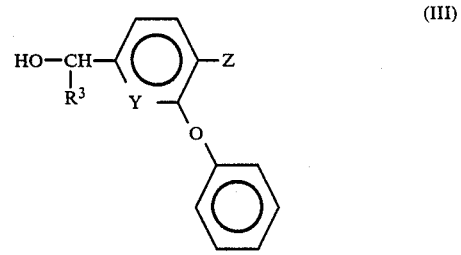

wherein $R^3$, Y and Z are as defined above.

The active compounds of the invention are well tolerated by plants, have a favourable level of toxicity to warm-blooded animals, and can be used for combating arthropod pests, especially insects or acarids, which are encountered in agriculture, in veterinary practice, in forestry, in the protection of stored products and of materials, and in the hygiene field. They are active against normally sensitive and resistant species and against all or some stages of development. The above-mentioned pests include *Lucilia cuprina* (the Australian sheep blowfly), *Blatella germanica* (German cockroach), *Heliothis punctigera* (cotton budworm), *Musca domestica* housefly, *Aedes Australis* Australian mosquito, *Periplaneta americana* American cockroach, *Pheidole megacephala* coastal brown ant, *Dermestes maculata* hide beetle, *Triboleum castaneum* flour beetle, *Stegobium paniceum*, drug store beetle and *Sitophilus oryzae* rice weevil.

The present invention also provides arthropodicial compositions containing as active ingredient(s) one or more compound(s) of the present invention.

The present invention also provides a method of combating arthropods (especially insects or acarids) which comprises applying to the arthropods, or to a habitat thereof, a compound of the present invention alone or in the form of a composition containing as active ingredient a compound of the present invention.

The present invention also provides a method of freeing or protecting domesticated animals from parasitical insects or acarids which comprises applying to said animals a compound according to the present invention, or a composition containing such a compound as the active ingredient.

In the compositions of this invention, the active compounds are converted into such customary formulations as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, and coating compositions for use on seed, as well as ULV cold mist and warm mist formulations.

These formulations may be produced in known manner, for example by mixing the active compounds with extenders, i.e., liquid or liquefied gaseous or solid diluents or carriers, optionally with the use of surface-active agents, i.e., emulsifying agents and/or dispersing agents and/or foam-forming agents. Where water is used as an extender, auxiliary solvents, such as for example, organic solvents, can also be used.

Examples of suitable liquid diluents or carriers, especially solvents, are aromatic hydrocarbons, such as xylene, toluene or alkyl naphthalenes, chlorinated aromatic or chlorinated aliphatic hydrocarbons, such as chlorobenzenes, chloroethylenes or methylene chloride; aliphatic or alicyclic hydrocarbons, such as cyclohexane or paraffins, for example mineral oil fractions; alcohols, such as butanol or glycol, as well as their ethers; and esters, ketones, such as acetone, methyl ethyl ketone, methyl isobutyl ketone or cyclohexanone; and strongly polar solvents, such as dimethylformamide and dimethyl sulphoxide, as well as water.

By liquefied gaseous diluents or carriers are meant liquids which would be gasesous at normal temperature and under normal pressure, for example aerosol propellants, such as halogenated hydrocarbons as well as butane, propane, nitrogen and carbon dioxide.

Examples of solid carriers are ground natural minerals, such as kaolins, clays, talc, chalk, quartz, attapulgite, montmorillonite or diatomaceous earth; and ground synthetic minerals, such as highly-dispersed silicic acid, alumina and silicates. As solid carriers for granules there may be used crushed and fractionated natural rocks such as calcite, marble, pumice, sepiolite and dolomite; as well as synthetic granules of inorganic and organic meals, and granules of organic material such as sawdust, coconut shells, maize cobs and tobacco stalks.

Examples of emulsifying and/or foam-forming agents are non-ionic and anionic emulsifiers, such as polyoxyethylene-fatty acid esters, polyoxy ethylene-fatty alcohol ethers, for example alkylaryl polyglycol ethers, alkyl sulphonates, alkyl sulphates, aryl sulphonates, as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is also possible to use colorants such as inorganic pigments, for example iron oxide, titanium oxide and Prussian Blue, and organic dyestuffs, such as alizarin dyestuffs, azo dyestuffs or metal phthalocyanine dyestuffs.

The formulations in general will contain from 0.01 to 99 percent by weight of active compound, preferably from 0.5 to 95 percent by weight.

The active compounds according to the invention may be used in the form of formulations of the types that are commercially available or in the use forms prepared from these formulations.

The active compound content of the use forms prepared from the formulations of the types that are commercially available can vary within wide ranges. Generally, the proportion of the active compound in such use forms can range from 0.0000001% (0.1 ppm) to 99.9% by weight, the preferred range being from 0.1 ppm to 10% by weight.

The compounds may be employed in a customary manner appropriate for the particular use forms.

The active compounds according to the invention are also suitable for combating ectoparasites and endoparasites in the field of veterinary medicine. The compounds may be used in a known manner, such as orally in the form of, for example, tablets, capsules, drenches and granules; dermally by means of, for example, dipping, spraying, pouring-on, spotting-on and powdering.

The compounds may be employed either as the sole toxic agent in compositions such as those described above, or in combination with other insecticides such as pyrethrum, rotenone, or with fungicidal or bactericidal agents, to provide compositions useful for household and agricultural dusts and sprays, textile coating and impregnation, and the like.

In particular, the compounds of the invention may be advantageously combined with other substances which have a synergistic or potentiating action. Generally such substances are of the class of microsomal oxidase inhibitors, i.e., they inhibit the detoxification of insecticides in insects produced by the action of oxidative enzymes. Typical substances of this type are the pyrethrin synergists of which the following are examples:

[2-(2-butoxyethoxy)ethoxy]-4,5-methylenedioxy-2-propyltoluene (Piperonyl butoxide), 3-hexyl-5(3,4-methylenedioxyphenyl)-2-cyclohexanone (Piperonyl cyclonene), 2-(3,4-methylenedioxy-phenoxy)-3,6,9-trioxaundecane (Sesoxane or Sesamex), 1,2-(methylenedioxy)-4-[2-(octylsulfinyl)propyl]benzene (Sulfoxide), dipropyl-5,6,7,8-tetrahydro-7-methylnaphtho-[2,3-d], 3-dioxole-5,6-dicarboxylate (n-Propyl isome), as well as propynyl ethers and propynyl oximes.

("Sesoxane", "Sesamex" and "Sulphoxide" are Registered Trade Marks).

Piperonyl butoxide is particularly useful as a potentiator. The amount of piperonyl butoxide used may vary from 1/1000th to fifty times the weight of the compound I the preferred range being from about 1/100th to five parts by weight. 'Sesamex' also is a useful potentiator in similar amounts.

The preparation and properties of the compounds of the invention are illustrated by the following specific examples. It should be noted, of couresst, that these examples are intended to be illustrative of the methods and procedures utilized in preparing the compounds and that they are not intended to be restrictive or to be regarded as embodying the only way in which the compounds can be formed and recovered.

EXAMPLE 1

α-Cyano-4'-fluoro-3'-phenoxybenzyl-1-(4-ethoxyphenyl)-2,2,3,3-tetrafluorocyclobutane-1-carboxylate 4-Fluoro-3-phenoxybenzaldehyde bisulphite salt (0.64 g) was slurried with water (5 ml) and KCN (0.26 g) added. This was followed by the addition of diethyl ether (5 ml) and the reaction mixture was stirred at room temperature for 1 hour. The layers were separated and the ether layer washed with water and evaporated to yield the 4-fluoro-3-phenoxybenzaldehyde cyanohydrin as a colourless oil which was used for the subsequent reaction without further purification.

1-(4-ethoxyphenyl)-2,2,3,3-tetrafluorocyclobutane-1-carboxylic acid (0.5 g) was refluxed with thionyl chloride (0.48 g), on a steam bath for 1 hour and then evaporated to dryness to yield the acid chloride as a colourless oil. This oil was dissolved in benzene (5 ml) and pyridine (0.24 ml) followed in 2 minutes by the above cyanohydrin dissolved in benzene (5 ml). The mixture was allowed to react at room temperature overnight, after which it was quenched in dilute HCl extracted several times with diethyl ether. The ether layer was washed with water, sodium bicarbonate and again with water. The solvent layer was dried with anhydrous sodium sulphate and evaporated to yield 0.97 g of the racemic ester product.

A sample of the racemic ester was separated into two pairs of diastereoisomeric forms by preparative high performance liquid chromatography (HPLC) using petroleum spirit (60°-80°)/ethyl acetate as the eluting solvents. The isomer pair eluting second is hereafter referred to as the compound of Example 1A. The first isomer pair eluted is hereafter referred to as the compound of Example 1B.

All three ester forms had identical infrared and mass spectra which were consistent with the stated structures.

Analysis: Found: C, 63.0; H, 4.1; F, 18.4; N, 3.0%. Calculated for: $C_{27}H_{20}F_5NO_4$ C, 62.7; H, 3.9; F 18.4; N 2.7%.

EXAMPLE 2

4'-fluoro-3'-phenoxybenzyl-1-(4-ethoxy-phenyl)-2,2,3,3-tetrafluorocyclobutane-1-carboxylate 1-(4-ethoxyphenyl)-2,2,3,3-tetrafluorocyclobutane-1-carboxylic acid (0.29 g) was refluxed with thionyl chloride (0.24 g), on a steam bath for 1 hour and then evaporated to dryness to yield the acid chloride as a colourless oil. This oil was dissolved in benzene (5 ml) and pyridine (0.12 g) followed in 5 minutes by 4-fluoro-3-phenoxybenzyl alcohol (0.24 g) dissolved in benzene (5 ml). The mixture was allowed to react at room temperature overnight, after which it was quenched in dilute HCl and extracted several times with diethyl ether. The ether extract was washed with water, sodium bicarbonate and again with water; it was then dried with anhydrous sodium sulphate and evaporated to yield 0.55 g of the racemic ester product as a pale yellow oil. This was purified by HPLC to yield 0.38 g of a faintly yellow viscous oil.

The purified oil had infrared, nmr, and mass spectra consistent with the stated structure.

Analysis: Found: C, 63.56; H, 4.3; F, 19.3%. Calculated for $C_{26}H_{21}F_5O_4$: C, 63.41; H, 4.3; F 19.3%.

EXAMPLE 3

α-Ethynyl-4'-fluoro-3'-phenoxybenzyl-1-(4-ethoxyphenyl)-2,2,3,3-tetrafluorocyclobutane-1-carboxylate 1-(4-ethoxyphenyl)-2,2,3,3-tetrafluorocyclobutane-1-carboxylic acid (0.44 g) was refluxed with thionyl chloride (0.36 g), on a steam bath for 1 hour and then evaporated to dryness to yield the acid chloride as a colourless oil. This oil was dissolved in benzene (2 ml) and pyridine (0.18 g) followed in 2 minutes by α-ethynyl-4-fluoro-3-phenoxybenzyl alcohol (0.36 g) dissolved in benzene (2 ml). The mixture was allowed to react at room temperature overnight, after which it was quenched in dilute HCl and extracted several times with diethyl ether. The ether layer was washed with water, sodium bicarbonate and again with water; it was then dried with anhydrous sodium sulphate and evaporated to yield 0.83 g of the racemic ester product, as a pale yellow viscous oil.

A sample of the racemic ester was separated into two pairs of diastereoisomeric forms by preparative high performance liquid chromatography (HPLC) using petroleum spirit (60°-80°)/ethyl acetate as the eluting solvents. The isomer pair eluting first is hereafter referred to as the compound of Example 3A. The second isomer pair eluted is hereafter referred to as the compound of Example 3B. Removal of the solvent from the fractions gave colourless viscous oils.

Both ester forms had identical infrared and mass spectra which were consistent with the stated structures.

Analysis: Found: C, 65.3; H, 4.25; F, 18.2%. Calculated for $C_{28}H_{21}F_5O_4$: C, 65.1; H, 4.10; F 18.4%.

EXAMPLE 4 CL Resolved (− −) and (− +) enantiomers of α-Ethynyl-4'-fluoro-3'-phenoxybenzyl-1-(4-ethoxyphenyl)-2,2,3,3-tetrafluorocyclobutane-1-carboxylate $[\alpha](-)$ 1-(4-ethoxyphenyl)-2,2,3,3-tetrafluorocyclobutane-1-carboxylic acid (0.29 g) was refluxed with thionyl chloride (0.24 g), on a steam bath for 1 hour and then evaporated to dryness to yield the acid chloride as a colourless oil. This oil was dissolved in benzene (2 ml) and pyridine (0.12 g) dissolved in benzene (1 ml) added followed in 2 minutes by the α-ethyl-4-fluoro-3-phenoxybenzyl alcohol (0.24 g) dissolved in benzene (2 ml). The mixture was allowed to react at room temperature overnight, after which it was quenched in dilute HCl and extracted several times with diethyl ether. The ether layer was washed with water, sodium bicarbonate and again with water; it was dried with anhydrous sodium sulphate and evaporated to yield 0.48 g of the mixed ester enantiomers as a pale yellow oil.

A sample of the mixed ester enantiomers was separated into two diastereoisomeric forms by preparative high performance liquid chromatography (HPLC) using petroleum spirit (60°-80°)/ethyl acetate as the eluting solvents. The enantiomer eluting first is hereafter referred to as the compound of Example 4A. The second enantiomer eluted is hereafter referred to as the compound of Example 4B. The two ester forms had nmr spectra consistent with the stated structure.

The enantiomers were further characterised by measurement of their optical rotation:

Compound of Example 4A $[\alpha]^{20}_{Na\ 589} = -36.34°$ in EtOH $c = 1.1\%$,

Compound of Example 4B $[\alpha]^{20}_{Na\ 589} = -10.23°$ in EtOH $c = 1.68\%$

EXAMPLE 5

6-Phenoxypyrid-2-ylmethyl 1-(4-ethoxyphenyl)-2,2,3,3-tetrafluorocyclobutane carboxylate To a stirred solution of 1-(4-ethoxyphenyl)-2,2,3,3-tetrafluorocyclobutane carbonyl chloride (0.76 gm, 1.54 mmole) in dry benzene (10 ml) was added a solution of 2-hydroxymethyl-6-phenoxypyridine (0.305 g) and pyridine (0.12 g) in dry benzene (15 ml). The mixture was stirred at room temperature for 16 hours then diluted with ether, washed twice with water, dried over $Na_2SO_4$ and concentrated in vacuo. Purification by high pressure liquid chromatography gave the ester as a colourless oil. IR (film) $\lambda_{max}$ 1741, 1606, 1591, 1575, 1500, 1490, 1450 cm$^{-1}$. N.m.r. (250 MHz) δ (CDCl$_3$) 1.42, t, 3H, J=7 Hz, CH$_3$; 2.90–3.08, m, 1H, cyclobutyl H; 3.44–3.64, m, 1H, cyclobutyl H; 4.02, q, 2H, J=7 Hz, CH$_2$CH$_3$; 5.10, 5.16, ABq, 2H, J=14.5 Hz, CH$_2$-O; 6.71–7.64, m, 13H, aromatic H's. Mass spectrum, m/z 476 (M$^+$ +1), 456 (M$^+$ −19).

Analysis: Found: C, 63.2; H, 4.5; F, 15.9; N, 3.1%. Calculated for $C_{25}H_{21}F_4NO_4$: C, 63.2; H, 4.5; F, 16.0; N, 3.0%.

EXAMPLE 6

Insecticidal activity was investigated against blowfly, *Lucilia cuprina*. The method used was as follows:

(a) The compounds were tested for activity against a susceptible strain.

The test compound was applied in acetone solution, 0.5 μl dispensed with a Drummond micropipette to the dorsum of the thorax of 2–3 day old males. Adult flies were fed on water and sugar-only and maintained at 25° C. and 60–70% RH. The mortalities were determined after 48 hours. Moribund flies were regarded as dead. The LD$_{50}$ values, in terms of concentration, were interpolated from the probit/log dose relation using a computer program.

(b) Potentiation

The compound was also tested on the insects described above in conjunction with the potentiator piperonyl butoxide by pretreating such insect with 1 μl of a 2% solution of the potentiator in acetone.

The mortalities were counted at 48 hours after treatment and compared with acetone and acetone/potentiator controls.

The LD$_{50}$ value was determined as described above.

About the same levels of potentiation were obtained when piperonyl butoxide was replaced by an equal amount of "Sesoxane".

Using the above method the following results were obtained.

| Compound of Example No. | LD$_{50}$ (μg/insect) Alone | LD$_{50}$ (μg/insect) With Synergist |
| --- | --- | --- |
| 1A | 0.008 | 0.00005 |
| 1B | 0.06 | 0.0008 |
| 2 | 0.083 | 0.0019 |
| 3A | 0.0017 | 0.00008 |
| 3B | 0.13 | 0.008 |
| 4A | 0.0019 | 0.00006 |
| 4B | 0.06 | 0.004 |
| 5 | 0.05 | 0.004 |

EXAMPLE 7

Insecticidal activity against the German cockroach (*Blatella germanica*) was determined using the following method:

The compound under test was applied in acetone solution at a range of concentrations. 0.5 μl was dispensed with a Drummond micropipette to the ventral thorax of adult cockroaches. The mortalities were determined after 48 hours. Moribund cockroaches were regarded as dead. The LD$_{50}$ values in terms of concentration were determined by probit analysis of the mortality/concentration data.

Using the above method the following results were obtained.

| Compound of Example No. | LD$_{50}$ (μg/insect) B. germanica |
| --- | --- |
| 1A | 0.03 |
| 1B | 0.022 |
| 2 | 0.12 |
| 3A | 0.02 |
| 3B | >4 |
| 4A | 0.02 |
| 4B | 0.14 |

EXAMPLE 8

Insecticidal activity against the cotton pest *Heliothis punctigera* was determined using the following method:

The compound under test was applied in acetone solution at a range of concentrations. 0.5 μl was dispensed with a Drummond micropipette to the dorsal surface of 3rd instar larvae. Each larva was held in a separate container and was fed on spinach and maintained at 25° C. and 60–70% RH. The mortalities were determined after 48 hours. Moribund larvae were regarded as dead. The LD$_{50}$ values in terms of concentration were determined by a probit analysis of the mortality/concentration data.

Using the above method the following results were obtained.

| Compound of Example No. | LD$_{50}$ (μg/insect) H. punctigera |
| --- | --- |
| 1A | 0.0056 |
| 1B | 0.009 |
| 2 | 0.05 |
| 3A | 0.006 |
| 3B | 1.94 |
| 4A | 0.005 |
| 4B | 0.27 |
| 5 | — |

We claim:

1. A compound having a formula (I) and isomeric forms thereof, wherein
R$^1$ is C$_{1-4}$ alkoxy;
R$^2$ is hydrogen;
R$^3$ is hydrogen, CN, or C≡CH;
Y is CH;
Z is F; and
X$^1$, X$^2$, X$^3$ and X$^4$ are fluoro.

2. An arthropodicial composition comprising an arthropodicidal effective amount of a compound as claimed in claim 1 in admixture with a diluent or carrier.

3. A method of combating arthropods which comprises applying to the arthropods, or to their habitat an arthropodicaially effective amount of a compound according to claim 1.

4. A method of freeing or protecting domesticated animals from parastitical insects or acarids which comprises applying to said animals or to their habitat an arthropodicidally effective amount of a compound according to claim 1 in admixture with a diluent or carrier.

5. A compound as claimed in claim 1 wherein $R^1$ is ethoxy.

6. A compound selected from the group consisting of:
(i) α-Cyano-4'-fluoro-3'-phenoxybenzyl-1-(4-ethoxyphenyl)-2,2,3,3-tetrafluorocyclo-butane-1-carboxylate;
(ii) 4'-Fluoro-3'-phenoxybenzyl-1-(4-ethoxyphenyl)-2,2,3,3-tetrafluorocyclobutane-1-carboxylate;
(iii) α-Ethynyl-4'-fluoro-3'-phenoxybenzyl-1-(4-ethoxyphenyl)-2,2,3,3-tetrafluorocyclo-butane-1-carboxylate; and their isomeric forms.

7. A compound as claimed in claim 6, which is 4'-fluoro-3'-phenoxybenzyl-1-(4-ethoxyphenyl)-2,2,3,3-tetrafluorocyclo-butane-1-carboxylate, or an isomeric form thereof.

8. A compound as claimed in claim 6, which is α-cyano-4'-fluoro-3-phenoxybenzyl-1-(4-ethoxyphenyl)-2,2,3,3-tetrafluoro-cyclobutane-1-carboxylate, or an isomeric form thereof.

9. A compound as claimed in claim 6, which is α-ethynyl-4'-fluoro-3'-phenoxybenzyl-1-(4-ethoxyphenyl)-2,2,3,3-tetra-fluorocyclobutane-1-carboxylate, or an isomeric form thereof.

* * * * *